US012767624B2

(12) United States Patent
Sun et al.

(10) Patent No.: US 12,767,624 B2
(45) Date of Patent: Oct. 20, 2026

(54) METHOD FOR PURIFYING CANNABINOID COMPOUNDS

(71) Applicant: Chengdu Baiyu Pharmaceutical Co., Ltd., Chengdu (CN)

(72) Inventors: Yi Sun, Chengdu (CN); Xuezhen Xu, Chengdu (CN); Jing Zhang, Chengdu (CN); Yonggang Wei, Chengdu (CN)

(73) Assignee: CHENGDU BAIYU PHARMACEUTICAL CO., LTD., Chengdu (CN)

( * ) Notice: Subject to any disclaimer, the term of this patent is extended or adjusted under 35 U.S.C. 154(b) by 553 days.

(21) Appl. No.: 18/253,877

(22) PCT Filed: Nov. 25, 2021

(86) PCT No.: PCT/CN2021/133191
§ 371 (c)(1),
(2) Date: May 22, 2023

(87) PCT Pub. No.: WO2022/111586
PCT Pub. Date: Jun. 2, 2022

(65) Prior Publication Data

US 2024/0018079 A1 Jan. 18, 2024

(30) Foreign Application Priority Data

Nov. 25, 2020 (CN) ......................... 202011327265.4

(51) Int. Cl.
*C07C 37/88* (2006.01)
*A61K 31/00* (2006.01)
*C07C 37/68* (2006.01)
*C07C 39/23* (2006.01)

(52) U.S. Cl.
CPC .......... *C07C 37/685* (2013.01); *A61K 31/658* (2023.05); *C07C 37/88* (2013.01); *C07C 39/23* (2013.01)

(58) Field of Classification Search
CPC ........ C07C 37/685; C07C 37/88; C07C 39/23
See application file for complete search history.

(56) References Cited

U.S. PATENT DOCUMENTS

| | | | |
|---|---|---|---|
| 9,643,958 | B2 | 5/2017 | Ishibashi et al. |
| 2020/0039908 | A1 | 2/2020 | Elsohly et al. |

FOREIGN PATENT DOCUMENTS

| | | | |
|---|---|---|---|
| CN | 109311838 A | 2/2019 | |
| CN | 109476625 A | 3/2019 | |
| WO | 2017216362 A1 | 12/2017 | |
| WO | 2020077153 A1 | 4/2020 | |
| WO | 2020232545 A1 | 11/2020 | |

OTHER PUBLICATIONS

Drake, David J., "Classical/Nonclassical Hybrid Cannabinoids: Southern Aliphatic Chain-Functionalized C-6β Methyl, Ethyl, and Propyl Analogues"; J. Med. Chem., vol. 41, 1998; pp. 3598-3608.
West, Steven J. et al., "Selective Ionophore-Based Optical Sensors for Ammonia Measurement in Air," Anal. Chem. vol. 64, 1992; pp. 533-540.
International Search Report for China application PCT/CN2021/133191 mailed Feb. 22, 2022; 4 pp.
Written Opinion for China application PCT/CN2021/133191 dated Feb. 22, 2022; 5 pp.
RN: 6195-80-0, 64846-13-5, 64846-18-0, 65598-39-2, 66250-94-0, 77155-61-4, 81039-71-6, 77183-79-0; STN Registry, Nov. 16, 1984.
Loev, Bernard et al., Cannabinoids. Structure—Activity Studies Related to 1,2-Dimethylheptyl Derivatives; Journal of Medicinal Chemistry; 1973, vol. 16, No. 11, pp. 1200-1206.
Turner, Carlton et al., Constituents of *Cannabis sativa* L. XVIII—Electron Voltage Selected Ion Monitoring Study of Cannabinoids; Biomedical Mass Spectrometry; 1980, vol. 7 No. 6; pp. 247-256.
Extended European Search Report for EP Application No. 21897086.1 dated Nov. 4, 2024; 3 pp.
Jung, Byunghyuck et al., Synthetic Strategies for (−)-Cannabidiol and Its Structural Analogs; Chemistry 2019; DOI: 10.1002/asia.201901179; 15 pp.
Pitt, Colin G et al., "General Synthesis of Side Chain Derivatives of Cannabinoids," J. Org. Chem., vol. 44, No. 5, 1979; pp. 677-683.

*Primary Examiner* — Sikarl A Witherspoon
(74) *Attorney, Agent, or Firm* — Armstrong Teasdale LLP

(57) ABSTRACT

Disclosed is a method for purifying cannabinoid compounds that enables cannabinoid compounds to be obtained more economically and with a better purification effect.

9 Claims, No Drawings

METHOD FOR PURIFYING CANNABINOID COMPOUNDS

CROSS-REFERENCE TO RELATED APPLICATION

This application is a U.S. national stage application of PCT/CN2021/133191, filed on Nov. 25, 2021, which claims priority to Chinese Patent Application No. 202011327265.4 filed on Nov. 25, 2020. Both applications are hereby expressly incorporated by reference in their entirety.

TECHNICAL FIELD

The present application relates to the field of compound purification, in particular to a method for purifying cannabinoid compounds.

BACKGROUND

Cannabinoid compounds have great application value in pharmaceuticals. For example, it has medical effect or potential for Lennox-Gastaut syndrome, tuberous sclerosis-associated epilepsy, autism, post-traumatic stress disorder, inflammatory heart disease, traumatic brain injury, colon cancer and other indications.

Cannabinoids obtained by synthesis and extraction include various impurities, and the cannabinoid compounds are usually separated and purified by chromatography. However, chromatography not only requires the use of a large amount of solvents in industrialization, but also the purification effect is difficult to meet expectations, greatly limiting the scale and efficiency of the separation method. In addition, most cannabinoid compounds are unstable and prone to rearrangement and oxidation at room temperature, which brings difficulties to the separation and storage of the cannabinoid compounds, particularly the most widely used cannabidiol (CBD) and tetrahydrocannabinol (THC).

There is a need for methods that are cost-effective and suitable for large-scale purification of cannabinoid compounds.

SUMMARY

The object of the present application is to provide a method for purifying cannabinoid compounds. Compared with the existing purification methods, the method has the features of good purification effect and is suitable for industrial production.

One or more embodiments of the present application provide a method for purifying cannabinoid compounds, stereoisomers, deuterated products or salts thereof, comprising:

$$A\text{-}(OH)_n \xrightarrow{\text{step 1}} A\text{-}(OG)_n \xrightarrow{\text{step 2}} A\text{-}(OH)_n$$

wherein,

A-$(OH)_n$ is:

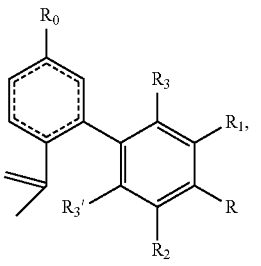

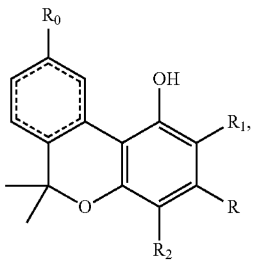

-continued

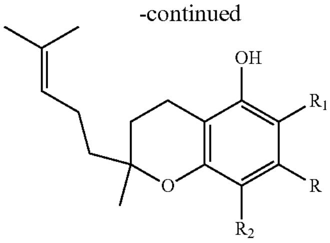

or

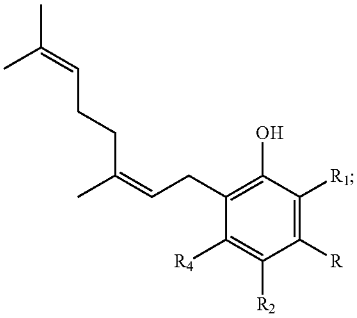

A-$(OG)_n$ is:

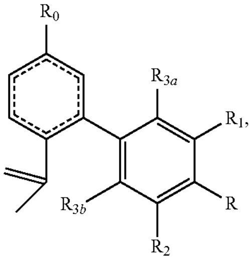

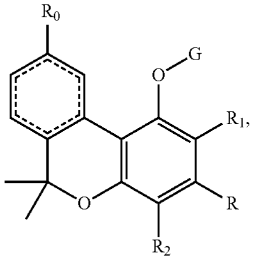

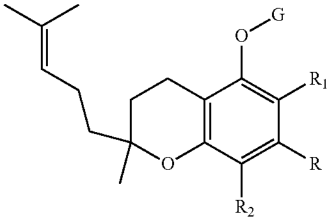

or

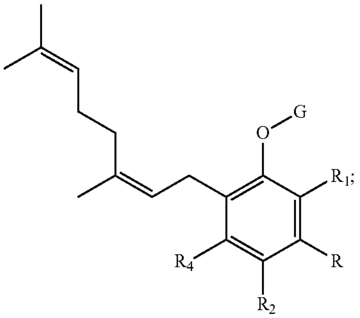

wherein:

$\overline{\overline{\ \ }}$ is a single bond or a double bond;

$R_0$ is $C_{1-6}$ alkyl or $C_{1-6}$ hydroxyalkyl;

R is H or $C_{1-12}$ alkyl;

$R_1$ is H or —COOH;

$R_2$ is H, —COOH or $C_{1-6}$ alkyl;

$R_3$ and $R_3'$ are each independently OH or $C_{1-6}$ alkoxy, and at least one of $R_3$ and $R_3'$ is $C_{1-6}$ alkoxy;

$R_4$ is OH, $C_{1-6}$ alkoxy, —COOH or —OCO$C_{1-6}$ alkyl; G is a silyl protecting group;

$R_{3a}$ and $R_{3b}$ are each independently —OG or $C_{1-6}$ alkoxy, and at least one of $R_{3a}$ and $R_{3b}$ is —OG;

n is 1 or 2.

In one or more embodiments, triethylchlorosilane is added in step 1.

In one or more embodiments, tetra-n-butylammonium fluoride is added in step 2.

In one or more embodiments,

A-$(OH)_n$ is:

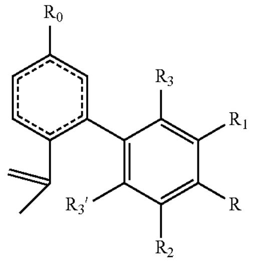

or

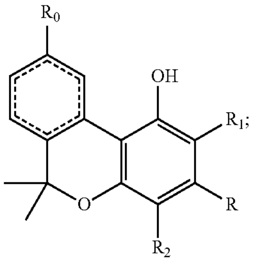

A-$(OG)_n$ is:

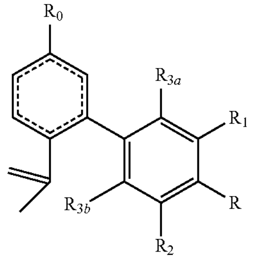

or

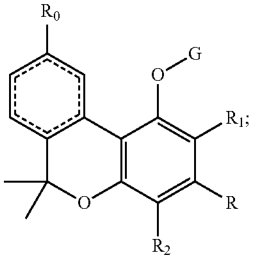

wherein:

$\overline{\underline{---}}$ is a single bond or a double bond;

$R_0$ is methyl or —$CH_2OH$;

R is H or $C_{1-8}$ alkyl;

$R_1$ is H or —COOH;

$R_2$ is H;

$R_3$ and $R_3'$ are each independently OH or —$OCH_3$, and at least one of $R_3$ and $R_3'$ is OH;

G is trimethylsilyl, triethylsilyl, triisopropylsilyl, tert-butyldimethylsilyl or tert-butyldiphenylsilyl;

$R_{3a}$ and $R_{3b}$ are each independently —OG or —$OCH_3$, and at least one of $R_{3a}$ and $R_{3b}$ is —OG;

n is 1 or 2.

In one or more embodiments,

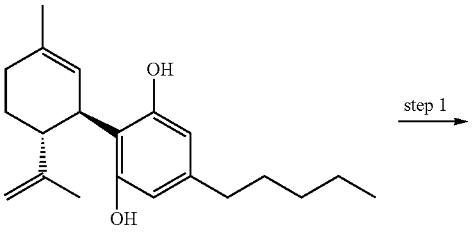

-continued

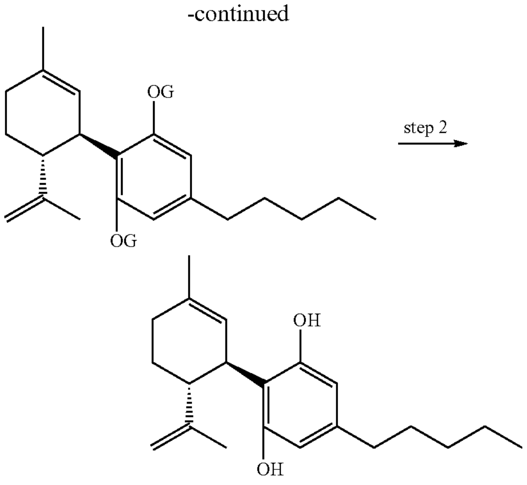

wherein:

G is triethylsilyl or tert-butyldimethylsilyl.

In one or more embodiments, the $C_{1-6}$ alkyl is methyl, and the $C_{1-6}$ hydroxyalkyl is —$CH_2OH$.

In one or more embodiments, the $C_{1-12}$ alkyl is pentyl.

In one or more embodiments, the pentyl is n-pentyl.

In one or more embodiments, the $C_{1-6}$ alkoxy is —$OCH_3$.

In one or more embodiments, the silyl protecting group is trimethylsilyl, triethylsilyl, triisopropylsilyl, tert-butyldimethylsilyl or tert-butyldiphenylsilyl.

In one or more embodiments, n is 2.

One or more embodiments of the present application provide compounds having the following structures:

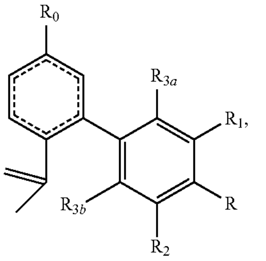

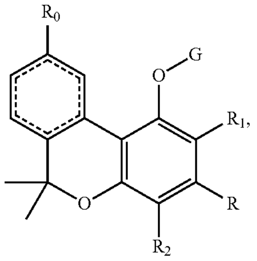

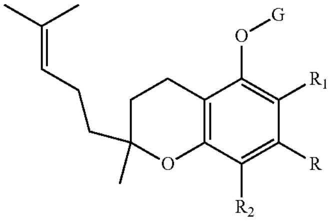

or

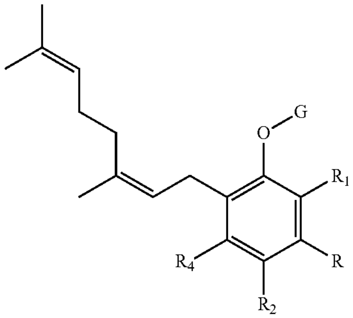

wherein,

=== is a single bond or a double bond;

$R_0$ is $C_{1-6}$ alkyl or $C_{1-6}$ hydroxyalkyl;

R is H or $C_{1-12}$ alkyl;

$R_1$ is H or —COOH;

$R_2$ is H, —COOH or $C_{1-6}$ alkyl;

$R_3$ and $R_3'$ are each independently OH or $C_{1-6}$ alkoxy, and at least one of $R_3$ and $R_3'$ is $C_{1-6}$ alkoxy;

$R_4$ is OH, $C_{1-6}$ alkoxy, —COOH or —$OCOC_{1-6}$ alkyl;

G is a silyl protecting group;

$R_{3a}$ and $R_{3b}$ are each independently —OG or $C_{1-6}$ alkoxy, and at least one of $R_{3a}$ and $R_{3b}$ is —OG.

In one or more embodiments, the $C_{1-6}$ alkyl is methyl, the $C_{1-6}$ hydroxyalkyl is —$CH_2OH$, the $C_{1-12}$ alkyl is pentyl, and the $C_{1-6}$ alkoxy is —$OCH_3$, the silyl protecting group is trimethylsilyl, triethylsilyl, triisopropylsilyl, tert-butyldimethylsilyl or tert-butyldiphenylsilyl.

In one or more embodiments:

=== is a single bond or a double bond;

$R_0$ is methyl or —$CH_2OH$;

R is H or $C_{1-8}$ alkyl;

$R_1$ is H or —COOH;

$R_2$ is H;

$R_3$ and $R_3'$ are each independently OH or —$OCH_3$, and at least one of $R_3$ and $R_3'$ is OH;

G is trimethylsilyl, triethylsilyl, triisopropylsilyl, tert-butyldimethylsilyl or tert-butyldiphenylsilyl;

$R_{3a}$ and $R_{3b}$ are each independently —OG or —$OCH_3$, and at least one of $R_{3a}$ and $R_{3b}$ is —OG.

Unless stated to the contrary, the terms used in the specification and claims have the following meanings.

The carbon, hydrogen or oxygen involved in the groups and compounds described in present application all include their isotopes, and which are optionally further replaced by one or more of their corresponding isotopes, wherein the isotopes of carbon include $^{12}C$, $^{13}C$ and $^{14}C$, and the isotopes of hydrogen include protium (H), deuterium (D, also called heavy hydrogen), tritium (T, also called super-heavy hydrogen), the isotopes of oxygen include $^{16}O$, $^{17}O$ and $^{18}O$.

"Alkyl" refers to a linear or branched chain saturated aliphatic hydrocarbon group of 1 to 20 carbon atoms (e.g. 1, 2, 3, 4, 5, 6, 7, 8, 9, 10, 11, 12, 13, 14, 15, 16, 17, 18, 19 or 20 carbon atoms), for example, an alkyl group of 1 to 8 carbon atoms, an alkyl group of 1 to 6 carbon atoms, or an alkyl group of 1 to 4 carbon atoms. Non-limiting examples include methyl, ethyl, n-propyl, isopropyl, n-butyl, sec-butyl, neobutyl, tert-butyl, n-pentyl, isopentyl, neopentyl, n-hexyl and its various branched isomers; when an alkyl group is substituted by a substituent, it may be optionally further substituted by one or more substituents.

"Hydroxyalkyl" refers to an alkyl group substituted with at least one hydroxy group. The alkyl is defined in the same way as for the "alkyl" described above.

"Alkoxy" refers to a group in which at least one carbon atom in an alkyl group is substituted by an oxygen atom. Non-limiting examples include methoxy, ethoxy, n-propoxy, isopropoxy, n-butoxy, sec-butoxy, tert-butoxy, n-pentoxy, n-hexyloxy, cyclopropoxy and cyclobutoxy. The definition of alkyl is the same as the definition of "alkyl" mentioned above.

"Stereoisomer" refers to isomers produced by different arrangements of atoms in a molecule in space, including cis-trans isomers, enantiomers and conformers.

"Optional", "optionally", "selective" or "selectively" means that the subsequently described event or circumstance may, but does not necessarily, occur, and the description includes cases where the event or circumstance occurs and cases where it does not. For example, "heterocyclyl optionally substituted with alkyl" means that the alkyl may, but does not necessarily, be present, and the description includes the case where the heterocyclyl is substituted with alkyl and the case where the heterocyclyl is not substituted with alkyl.

The specification of the present application has described specific embodiments in detail, and those skilled in the art should recognize that the above-mentioned embodiments are exemplary and should not be construed as limitations of the present application. For those skilled in the art, on the premise of not departing from the principles of the present application, some improvements and modifications are made to the present application, and the technical solutions obtained by these improvements and modifications also fall within the protection scope of the claims of the present application.

DETAILED DESCRIPTION

The following examples illustrate the technical schemes of the present application in detail, but the protection scope of the present application includes but is not limited thereto.

Example 1

(1'R,2'R)-5'-methyl-4-pentyl-2'-(prop-1-en-2-yl)-1',2',3',4'-tetrahydro-[1,1'-biphenyl]-2,6-diol (Compound 1)

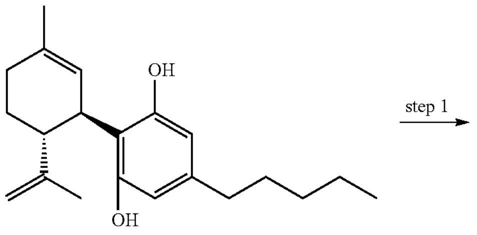

1a

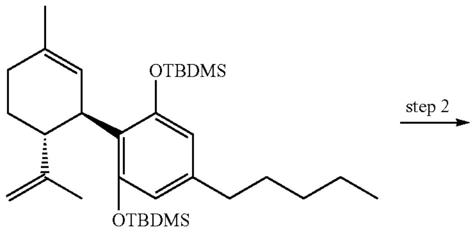

1b

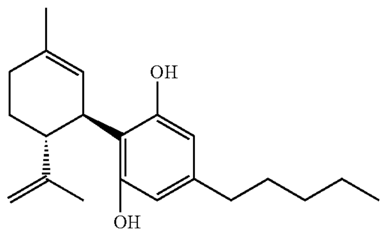

1

Step 1:

(((1'R,2'R)-5'-methyl-4-pentyl-2'-(prop-1-en-2-yl)-1',2',3',4'-tetrahydro-[1,1'-biphenyl]-2,6-diyl)bis(oxy))bis(tert-butyldimethylsilane) (1b)

(1'R,2'R)-5'-methyl-4-pentyl-2'-(prop-1-en-2-yl)-1',2',3',4'-tetrahydro-[1,1'-biphenyl]-2,6-diol 1a mixed with impurities (crude product of Compound 1) (0.1 g) and imidazole (87 mg, 1.28 mmol) were dissolved in dichloromethane (0.7 ml), and tert-butyldimethylsilyl chloride (TBDMSCl) (116 mg, 0.76 mmol) was added at 0° C., which was reacted at 40° C. for 3 hours. TLC detected that the reaction was completed, and then the reaction was stopped. The solvent was removed by rotary evaporation, and separated and purified by silica gel column chromatography (dichloromethane/n-hexane (v/v)=1/19) to obtain the title compound (((1'R,2'R)-5'-methyl-4-pentyl-2'-(prop-1-en-2-yl)-1',2',3',4'-tetrahydro-[1,1'-biphenyl]-2,6-diyl)bis(oxy))bis(tert-butyldimethylsilane) 1 b (146 mg, 84% yield, pale yellow oil).

$^1$H NMR (300 MHz, Chloroform-d) δ 6.19 (s, 2H), 5.22 (t, 1H), 4.45-4.52 (m, 2H), 3.89-3.94 (m, 1H), 3.02 (td, 1H), 2.39-2.44 (m, 2H), 1.94-2.14 (m, 2H), 1.66-1.78 (m, 2H), 1.44-1.61 (m, 8H), 1.24-1.34 (m, 6H), 0.84-1.05 (s, 21H), 0.15-0.23 (m, 12H).

LC-MS m/z (ESI)=543.45 [M+1].

Step 2:

(1'R,2'R)-5'-methyl-4-pentyl-2'-(prop-1-en-2-yl)-1',2',3',4'-tetrahydro-[1,1'-biphenyl]-2,6-diol (Compound 1)

(((1'R,2'R)-5'-methyl-4-pentyl-2'-(prop-1-en-2-yl)-1',2',3',4'-tetrahydro-[1,1'-biphenyl]-2,6-diyl)bis(oxy))bis(tert-butyldimethylsilane) 1b (146 mg, 0.27 mmol) was dissolved in dichloromethane (1 ml), tetrahydrofuran solution of tetra-n-butylammonium fluoride (0.54 ml, 0.54 mmol) was added at 0° C., and which was reacted at 0° C. for 30 minutes. TLC detected that the reaction was completed, and then the reaction was stopped. The solvent was removed by rotary evaporation, and separated and purified by silica gel column chromatography (ethyl acetate/n-hexane (v/v)=2/8) to obtain the title compound (1'R,2'R)-5'-methyl-4-pentyl-2'-(prop-1-en-2-yl)-1',2',3',4'-tetrahydro-[1,1'-biphenyl]-2,6-diol (Compound 1) (80 mg, 95% yield, >99% purity, white solid).

$^1$H NMR (300 MHz, DMSO-d6) δ 8.61 (s, 2H), 5.99 (s, 2H), 5.06 (s, 1H), 4.38-4.47 (m, 2H), 3.80 (d, 1H), 2.96-3.04 (m, 1H), 2.25-2.30 (m, 2H), 1.86-2.07 (m, 2H), 1.42-1.64 (m, 10H), 1.20-1.28 (m, 4H), 0.83 (t, 3H).

LC-MS m/z (ESI)=315.47 [M+1].

Example 2

(1'R,2'R)-5'-methyl-4-pentyl-2'-(prop-1-en-2-yl)-1',2',3',4'-tetrahydro-[1,1'-biphenyl]-2,6-diol (Compound 1)

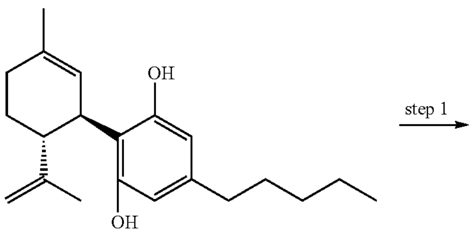

1a

-continued

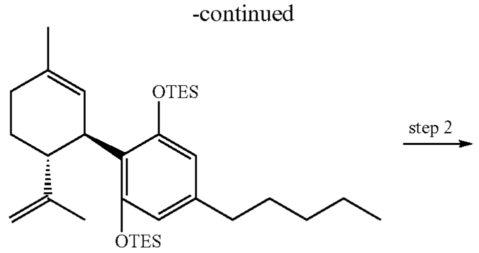

1c

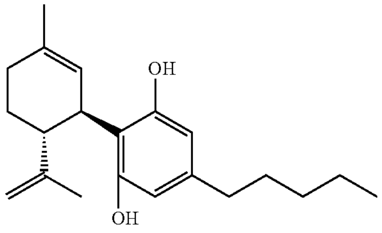

1

Step 1

(((1'R,2'R)-5'-methyl-4-pentyl-2'-(prop-1-en-2-yl)-1',2',3',4'-tetrahydro-[1,1'-biphenyl]-2,6-diyl)bis(oxy))bis(triethylsilane) (1c)

(1'R,2'R)-5'-methyl-4-pentyl-2'-(prop-1-en-2-yl)-1',2',3',4'-tetrahydro-[1,1'-biphenyl]-2,6-diol 1a mixed with impurities (crude product of Compound 1) (0.26 g) and imidazole (0.17 g, 2.5 mmol) were dissolved in dichloromethane (1.8 ml), and triethylchlorosilane (TESCl) (320 mg, 2.1 mmol) was added at 0° C., which was reacted at 40° C. for 3 hours. TLC detected that the reaction was completed, and then the reaction was stopped. The solvent was removed by rotary evaporation, and separated and purified by silica gel column chromatography (dichloromethane/n-hexane (v/v)=1/19) to obtain the title compound (((1'R,2'R)-5'-methyl-4-pentyl-2'-(prop-1-en-2-yl)-1',2',3',4'-tetrahydro-[1,1'-biphenyl]-2,6-diyl)bis(oxy))bis(triethylsilane) 1c (433 mg, 99% yield, pale yellow oil).

$^1$H NMR (300 MHz, Chloroform-d) δ 6.16 (s, 2H), 5.19 (s, 1H), 4.45-4.49 (m, 2H), 3.85-3.89 (m, 1H), 2.91-2.99 (m, 1H), 2.42 (t, 2H), 1.94-2.14 (m, 2H), 1.48-1.79 (m, 12H), 1.18-1.35 (m, 4H), 0.69-0.99 (m, 33H).

LC-MS m/z (ESI)=543.45 [M+1].

Step 2:

(1'R,2'R)-5'-methyl-4-pentyl-2'-(prop-1-en-2-yl)-1',2',3',4'-tetrahydro-[1,1'-biphenyl]-2,6-diol (Compound 1)

(((1'R,2'R)-5'-methyl-4-pentyl-2'-(prop-1-en-2-yl)-1',2',3',4'-tetrahydro-[1,1'-biphenyl]-2,6-diyl)bis(oxy))bis(triethylsilane) (1c) (433 mg, 0.8 mmol) was dissolved in anhydrous tetrahydrofuran (4 ml), tetrahydrofuran solution of tetra-n-butylammonium fluoride (1.8 ml, 1.8 mmol) was added at 0° C., and which was reacted at 0° C. for 30 minutes. TLC detected that the reaction was completed, and then the reaction was stopped. The solvent was removed by rotary evaporation, and separated and purified by silica gel column chromatography (ethyl acetate/n-hexane (v/v)=2/8) to obtain the title compound (1'R,2'R)-5'-methyl-4-pentyl-2'-(prop-1-en-2-yl)-1',2',3',4'-tetrahydro-[1,1'-biphenyl]-2,6-diol (Compound 1) (250 mg, 99% yield, >99% purity, white solid).

$^1$H NMR (300 MHz, DMSO-d6) δ 8.61 (s, 2H), 5.99 (s, 2H), 5.06 (s, 1H), 4.38-4.47 (m, 2H), 3.80 (d, 1H), 2.96-3.04 (m, 1H), 2.25-2.30 (m, 2H), 1.86-2.07 (m, 2H), 1.42-1.64 (m, 10H), 1.20-1.28 (m, 4H), 0.83 (t, 3H).

LC-MS m/z (ESI)=315.47 [M+1].

What is claimed is:

1. A method for purifying cannabinoid compounds, stereoisomers, deuterated products or salts thereof, comprising:

$$A\text{-}(OH)_n \xrightarrow{\text{step 1}} A\text{-}(OG)_n \xrightarrow{\text{step 2}} A\text{-}(OH)_n$$

wherein,

A-(OH)$_n$ is

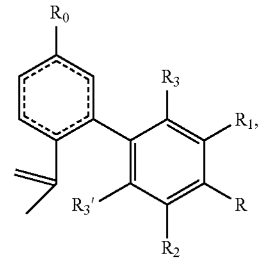

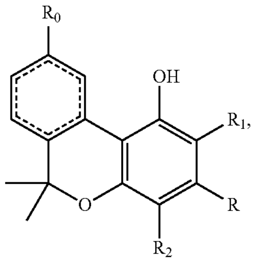

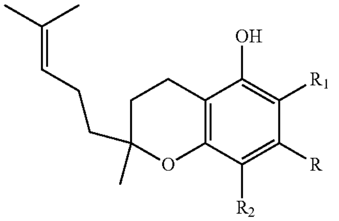

or

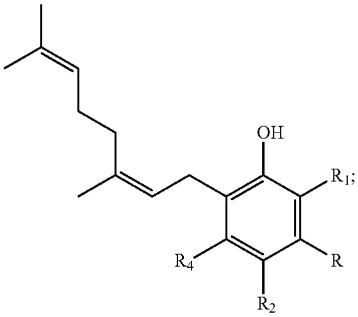

A-(OG)$_n$ is:

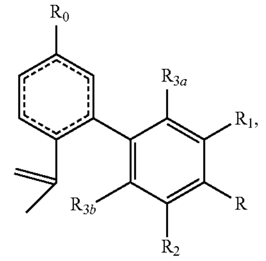

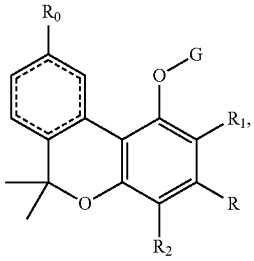

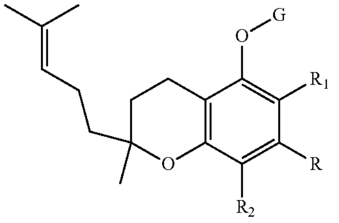

or

-continued

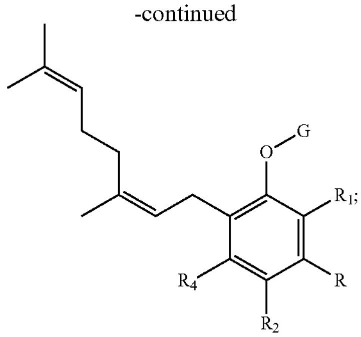

wherein, $\overset{---}{=}$ is a single bond or a double bond;

$R_0$ is $C_{1-6}$ alkyl or $C_{1-6}$ hydroxyalkyl;

R is H or $C_{1-12}$ alkyl;

$R_1$ is H or —COOH;

$R_2$ is H, —COOH or $C_{1-6}$ alkyl;

$R_3$ and $R_3'$ are each independently OH or $C_{1-6}$ alkoxy, and at least one of $R_3$ and $R_3'$ is $C_{1-6}$ alkoxy;

$R_4$ is OH, $C_{1-6}$ alkoxy, —COOH or —$OCOC_{1-6}$ alkyl;

G is a silyl protecting group;

$R_{3a}$ and $R_{3b}$ are each independently —OG or $C_{1-6}$ alkoxy, and at least one of $R_{3a}$ and $R_{3b}$ is —OG;

n is 1 or 2.

2. The method for purifying cannabinoid compounds according to claim 1, wherein A-(OH)$_n$ is:

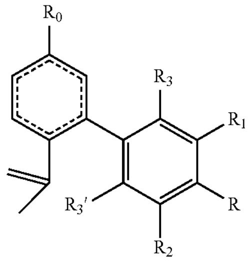

or

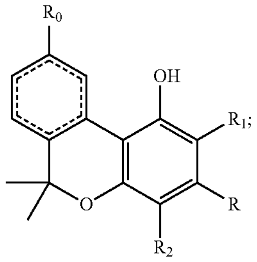

A-(OG)$_n$ is:

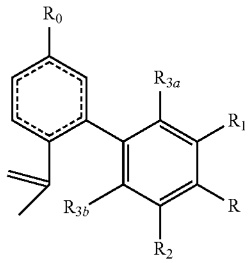

or

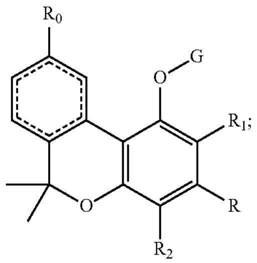

wherein:

$\overset{---}{=}$ is a single bond or a double bond;

$R_0$ is methyl or —$CH_2OH$;

$R_1$ is H or $C_{1-8}$ alkyl;

$R_1$ is H or —COOH;

$R_2$ is H;

$R_3$ and $R_3'$ are each independently OH or —$OCH_3$, and at least one of $R_3$ and $R_3'$ is OH;

G is trimethylsilyl, triethylsilyl, triisopropylsilyl, tert-butyldimethylsilyl or tert-butyldiphenylsilyl;

$R_{3a}$ and $R_{3b}$ are each independently —OG or —$OCH_3$, and at least one of $R_{3a}$ and $R_{3b}$ is —OG;

n is 1 or 2.

3. The method for purifying cannabinoid compounds according to claim 1, wherein

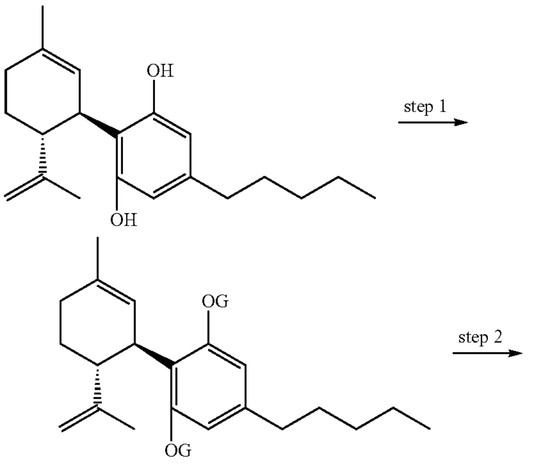

-continued

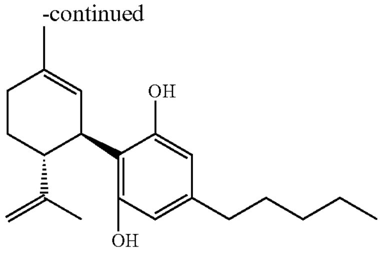

wherein:

G is triethylsilyl or tert-butyldimethylsilyl.

4. The method for purifying cannabinoid compounds according to claim 1, wherein the $C_{1-6}$ alkyl is methyl, and the $C_{1-6}$ hydroxyalkyl is —$CH_2OH$.

5. The method for purifying cannabinoid compounds according to claim 1, wherein the $C_{1-12}$ alkyl is pentyl.

6. The method for purifying cannabinoid compounds according to claim 1, wherein the $C_{1-6}$ alkoxy is —$OCH_3$.

7. The method for purifying cannabinoid compounds according to claim 1, wherein the silyl protecting group is trimethylsilyl, triethylsilyl, triisopropylsilyl, tert-butyldimethylsilyl or tert-butyldiphenylsilyl.

8. The method for purifying cannabinoid compounds according to claim 1, wherein n is 2.

9. The method for purifying cannabinoid compounds according to claim 5, wherein the pentyl is n-pentyl.

* * * * *